United States Patent
Elhawary et al.

(10) Patent No.: US 10,675,105 B2
(45) Date of Patent: *Jun. 9, 2020

(54) CONTROLLER DEFINITION OF A ROBOTIC REMOTE CENTER OF MOTION

(71) Applicant: KONINKLIJKE PHILIPS N.V., Eindhoven (NL)

(72) Inventors: Haytham Elhawary, New York, NY (US); Aleksandra Popovic, Boston, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 138 days.

This patent is subject to a terminal disclaimer.

(21) Appl. No.: 15/918,648

(22) Filed: Mar. 12, 2018

(65) Prior Publication Data
US 2018/0200013 A1    Jul. 19, 2018

Related U.S. Application Data

(63) Continuation of application No. 15/470,523, filed on Mar. 27, 2017, now Pat. No. 9,913,696, which is a continuation of application No. 14/418,593, filed as application No. PCT/IB2013/056336 on Aug. 2, 2013, now Pat. No. 9,603,666.

(60) Provisional application No. 61/678,708, filed on Aug. 2, 2012.

(51) Int. Cl.
*G06F 19/00* (2018.01)
*A61B 34/30* (2016.01)
(Continued)

(52) U.S. Cl.
CPC ............ *A61B 34/30* (2016.02); *A61B 1/0016* (2013.01); *A61B 1/00163* (2013.01);
(Continued)

(58) Field of Classification Search
CPC ........ A61B 19/2203; A61B 2019/2211; A61B 2019/2292; A61B 2019/461
See application file for complete search history.

(56) References Cited

U.S. PATENT DOCUMENTS

| 5,279,309 A | 1/1994 | Taylor |
| 6,493,608 B1 | 12/2002 | Niemeyer |
| (Continued) | | |

FOREIGN PATENT DOCUMENTS

| JP | 2007050270 A | 3/2007 |
| WO | 2011088400 A2 | 1/2010 |
| (Continued) | | |

OTHER PUBLICATIONS

Lona Vyas et al "Flexible Robotics", BJU International, 107, pp. 187-189, doi: 10.1111/i.1464-410X.2010.09886,09894.x.

*Primary Examiner* — Ian Jen

(57) ABSTRACT

A robotic surgical system employs a surgical instrument (20), a robot (40) for navigating the surgical instrument (20) relative to an anatomical region (10) within a coordinate system (42) of the robot (40), and a robot controller (43) for defining a remote center of motion for a spherical rotation of the surgical instrument (20) within the coordinate system (42) of the robot (40) based on a physical location within the coordinate system (42) of the robot (40) of a port (12) into the anatomical region (10). The definition of the remote center of rotation is used by the robot controller (43) to command the robot (40) to align the remote center of motion of the surgical instrument (20) with the port (12) into the anatomical region (10) for spherically rotating the surgical instrument (20) relative to the port (12) into the anatomical region (10).

5 Claims, 6 Drawing Sheets

(51) Int. Cl.
*A61B 34/00* (2016.01)
*A61B 90/00* (2016.01)
*A61B 1/00* (2006.01)
*B25J 9/16* (2006.01)

(52) U.S. Cl.
CPC .............. *A61B 34/76* (2016.02); *A61B 90/06* (2016.02); *B25J 9/1689* (2013.01); *A61B 2034/301* (2016.02); *A61B 2090/061* (2016.02); *A61B 2090/065* (2016.02); *A61B 2090/066* (2016.02); *G05B 2219/45118* (2013.01)

(56) References Cited

U.S. PATENT DOCUMENTS

| | | | |
|---|---|---|---|
| 7,021,173 B2 | 4/2006 | Stoianovici | |
| 7,725,214 B2 | 5/2010 | Diolaiti | |
| 2002/0169440 A1 | 11/2002 | Jensen | |
| 2007/0018958 A1* | 1/2007 | Tavakoli | B25J 3/04 345/161 |
| 2007/0173975 A1 | 7/2007 | Schena | |
| 2009/0326531 A1* | 12/2009 | Geiselhart | A61B 18/1447 606/52 |
| 2010/0280437 A1 | 11/2010 | Murr | |
| 2011/0028992 A1* | 2/2011 | Geiger | B25J 9/1664 606/130 |
| 2011/0034924 A1* | 2/2011 | Tan | A61B 17/6425 606/59 |
| 2012/0226277 A1* | 9/2012 | Tan | A61B 17/6425 606/59 |
| 2015/0161802 A1 | 6/2015 | Christiansen | |
| 2018/0200013 A1* | 7/2018 | Elhawary | A61B 34/30 |

FOREIGN PATENT DOCUMENTS

| | | |
|---|---|---|
| WO | 2010130817 A1 | 11/2010 |
| WO | 2011100110 A1 | 8/2011 |

* cited by examiner

CONTROLLER DEFINITION OF A ROBOTIC REMOTE CENTER OF MOTION

CROSS-REFERENCE TO PRIOR APPLICATIONS

This application is a continuation of U.S. patent application Ser. No. 15/470,523, filed Mar. 27, 2017, which is a continuation of U.S. Ser. No. 14/418,593, filed Jan. 30, 2015, now U.S. Pat. No. 9,603,666, issued on Mar. 28, 2017, which is the U.S. National Phase application under 35 U.S.C. § 371 of International Application No. PCT/IB2013/056336, filed on Aug. 2, 2013, which claims the benefit of U.S. Provisional Patent Application No. 61/678,708, filed on Aug. 2, 2012. These applications are hereby incorporated by reference herein.

The present invention generally relates to robotic control of a spherical rotation of a surgical instrument about a fulcrum point relative to an anatomical port during minimally invasive surgery. The present invention specifically relates to a definition by a robot controller of a remote center of motion for the surgical instrument at the anatomical port during the minimally invasive surgery.

Minimally invasive surgery is performed using one or more elongated surgical instruments inserted into a patient's body through small port(s). Of particular importance, a main visualization method for the minimally invasive surgery is an endoscope inserted into the patient's body through one of the small ports.

In robotic guided minimally invasive surgery, one or more of the surgical instruments are held and controlled by a robotic device as the surgical instruments are inserted through the small ports. More particularly, the small ports that are placed on the patient's body are the only incision points through which the surgical instruments may pass through to access the inside of the patient. As such, the surgical instruments may rotate around these fulcrum points, but the surgical instrument cannot impose translational forces on the ports as this would cause injury and harm to the patient. This is especially important for robotic guided surgery, because the robot has potential to exert large translational forces on the ports.

Some robots implement what is known as a remote center of motion ("RCM") at a mechanical fulcrum point of a surgical instrument whereby the robot may only enforce rotation at the small port and all translational forces at the small port are eliminated. As known in the art, the RCM for a surgical instrument may be achieved by implementing a mechanical design of the robot that has a fixed RCM for the surgical instrument at a specific location within a coordinate system of the robot. For example, FIG. 1 illustrates a robot 30 having an end effector 31 holding an endoscope 20. The mechanical design of robot 30, particularly end effector 31, provides for a fixed RCM 32 for endoscope 20. During a minimally invasive surgery, RCM 32 is aligned with a small port of an anatomical region 10 of a patient within a coordinate frame 33 of robot 30 as shown in FIG. 1. This alignment facilitates a spherical rotation of endoscope 20 about RCM 32 without any significant translational forces being exerted on the small port.

For robotic devices that do not have a remote center of motion inherent in the mechanism design, a robot controller must have the capability of defining a virtual remote center of motion is located in space in the coordinate frame of the robotic device and must have the capability to calculate the necessary motions of the robot in order to position the RCM in a manner that coincides with the anatomical port while avoiding any exertion of translational forces at that point in space. For example, as shown in FIG. 2, a robot 40 has an end effector 41 holding endoscope 20. Robot 40 does not have a mechanical RCM. A virtual RCM 21 for endoscope 20 therefore has to be defined for endoscope 20, which is navigated by robot 40 whereby virtual RCM 21 coincides with a port into anatomical region 10.

To this end, the present invention provides robotic surgical systems, robot controllers and robotic surgical methods for defining a virtual RCM in the coordinate frame of a robot and for aligning the virtual RCM with an anatomical port in an easy and non-disruptive manner.

One form of the present invention is a robotic surgical system employing a surgical instrument, a robot for navigating the surgical instrument relative to an anatomical region within a coordinate system of the robot, and a robot controller for defining a remote center of motion for a spherical rotation of the surgical instrument within the coordinate system of the robot based on a physical location within the coordinate system of the robot of a port into the anatomical region. The definition of the remote center of rotation is used by the robot controller to command the robot to align the remote center of motion of the surgical instrument with the port into the anatomical region for spherically rotating the surgical instrument relative to the port into the anatomical region.

In various embodiments of the robotic surgical system, the robot controller may defines the virtual remote center of motion by using a string potentiometer attached to the robot end effector, by locating the end effector tip at the port location, by using optical shape sensing fiber attached to the robot end effector, or by using compliance control of the robot and mathematical extraction of the remote center of motion.

A second form of the present invention includes a robotic surgical method involving a definition of a remote center of motion for a spherical rotation of a surgical instrument within a coordinate system of a robot based on a physical location within the coordinate system of the robot of a port into an anatomical region. The method further involves an alignment of the remote center of motion of the surgical instrument with the port into the anatomical region for spherically rotating the surgical instrument relative to the port into the anatomical region.

The foregoing forms and other forms of the present invention as well as various features and advantages of the present invention will become further apparent from the following detailed description of various embodiments of the present invention read in conjunction with the accompanying drawings. The detailed description and drawings are merely illustrative of the present invention rather than limiting, the scope of the present invention being defined by the appended claims and equivalents thereof.

Figure 1:
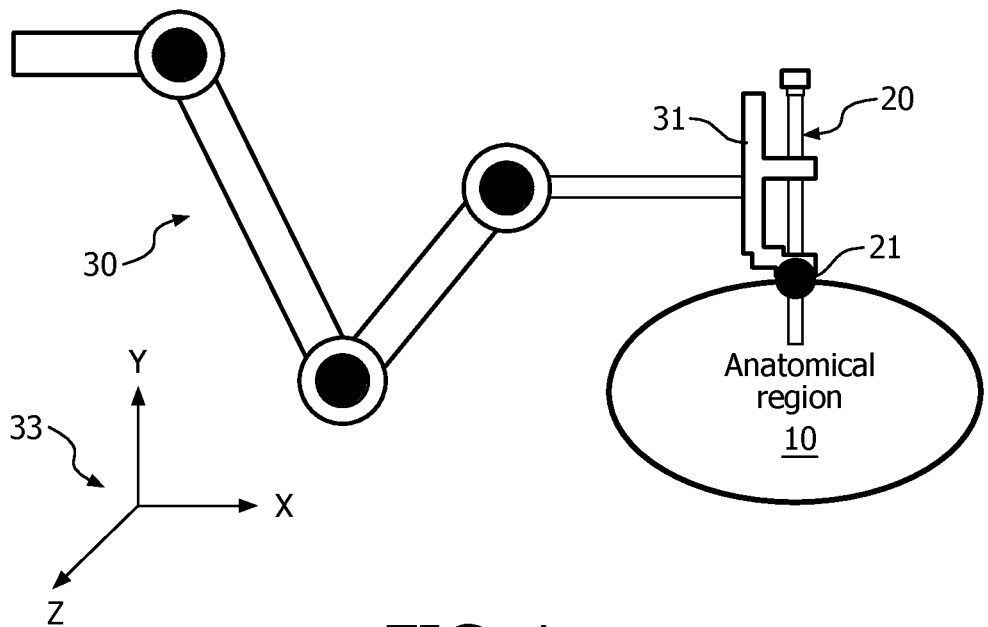
FIG. 1 illustrates an exemplary embodiment of a mechanical remote center of motion as known in the art.
Figure 2:
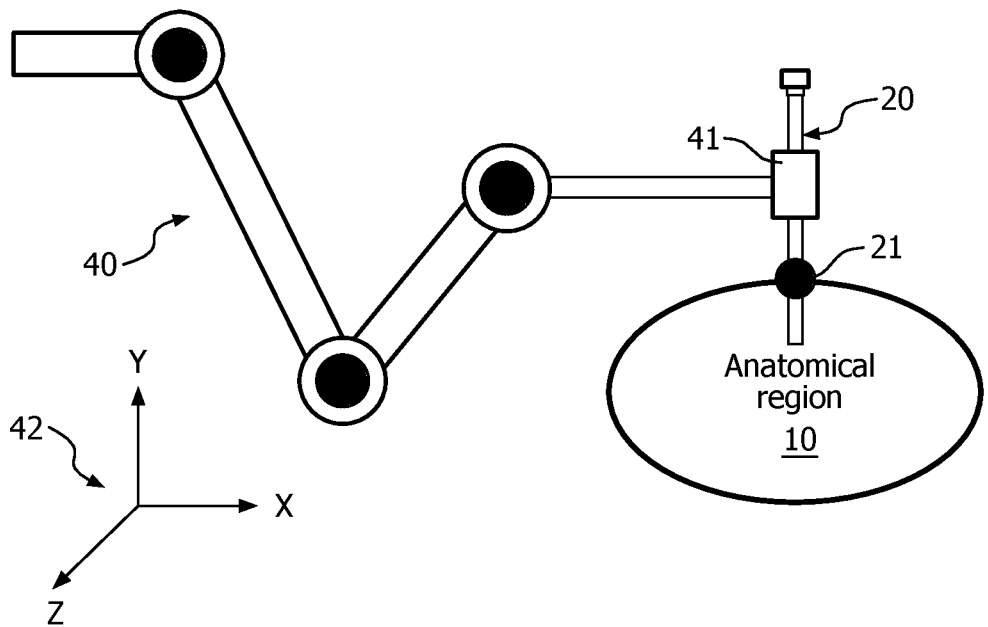
FIG. 2 illustrates an exemplary embodiment of a virtual remote center of motion in accordance with the present invention.
Figure 3:
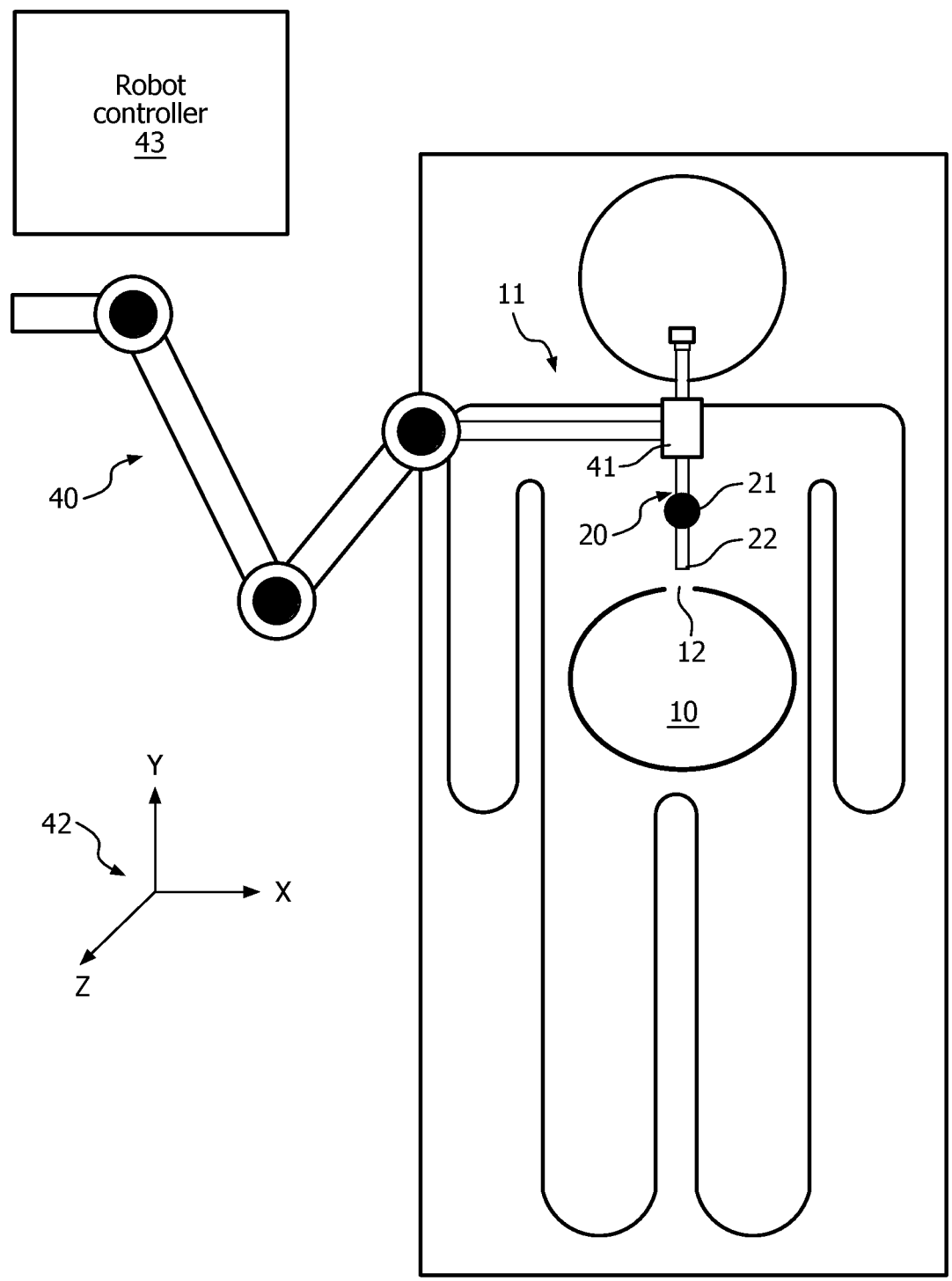
FIG. 3 illustrates an exemplary embodiment of a robotic surgical system in accordance with the present invention.

As shown in FIG. 3, a robotic surgical system of the present invention employs robot 40, a surgical instrument in the form of endoscope 20 and a robot controller 43 for any type of medical procedure including, but not limited to, minimally invasive cardiac surgery (e.g., coronary artery bypass grafting or mitral valve replacement), minimally invasive abdominal surgery (laparoscopy) (e.g., prostatectomy or cholecystectomy), and natural orifice translumenal endoscopic surgery.

Robot 40 is broadly defined herein as any robotic device structurally configured with motorized control of one or more joints for maneuvering an end-effector 41 as desired for the particular medical procedure. In practice, robot 40 may have a minimum of five (5) degrees-of-freedom including an end-effector translation, an end-effector axis rotation, and three (3) degrees of rotational freedom of the joints.

Endoscope 20 is broadly defined herein as any device having a field-of-view for imaging within anatomical region 10. Examples of endoscope 20 for purposes of the present invention include, but are not limited to, any type of scope, flexible or rigid (e.g., endoscope, arthroscope, bronchoscope, choledochoscope, colonoscope, cystoscope, duodenoscope, gastroscope, hysteroscope, laparoscope, laryngoscope, neuroscope, otoscope, push enteroscope, rhinolaryngoscope, sigmoidoscope, sinuscope, thorascope, etc.) and any device similar to a scope that is equipped with an image system (e.g., a nested cannula with imaging). The imaging is local, and surface images may be obtained optically with fiber optics, lenses, or miniaturized (e.g. CCD based) imaging systems.

In practice, endoscope 20 is mounted to end-effector 41 of robot 40. A pose of end-effector 41 41 of robot 40 is a position and an orientation of end-effector 41 within a coordinate system 42 of robot 40. With endoscope 20 being inserted within anatomical region 10, any given pose of the field-of-view of endoscope 20 within the anatomical region 10 corresponds to a distinct pose of end-effector 41 within the robotic coordinate system 42. Consequently, each individual endoscopic image generated by endoscope 20 within the anatomical region 10 may be linked to a corresponding pose of endoscope 20 within the anatomical region 10.

Robot controller 43 is broadly defined herein as any controller structurally configured to provide commands (not shown) to robot 40 for controlling a pose of end-effector 41 of robot 40 as desired for navigating endoscope 20 through a port 12 of anatomical region and for spherically rotating endoscope 20 about a virtual fulcrum point 21 upon a positioning of virtual fulcrum point 21 in a manner than partially or entirely coincides with port 12. For purposes of the present invention, a spherical rotation of endoscope 20 about virtual fulcrum point 21 is broadly defined as any rotational motion of endoscope 20 about virtual fulcrum point 21 in a fixed location of robotic coordinate system 42 without any significant wobble of endoscope 20 against port 12.

In operation, robot controller 43 executes various robotic surgical methods of the present invention to a define a virtual remote center of motion for the spherical rotation endoscope 20 within robotic coordinate system 42 based on a physical location within robotic coordinate system 42 of anatomical port 12 and to align the remote center of motion of endoscope 20 with anatomical port 12 for spherically rotating endoscope 20 relative to anatomical port 12. A description of various methods represented by flowcharts shown in FIGS. 4-7 will now be described herein to facilitate an understanding of the operation of robot controller 43.

Figure 4:
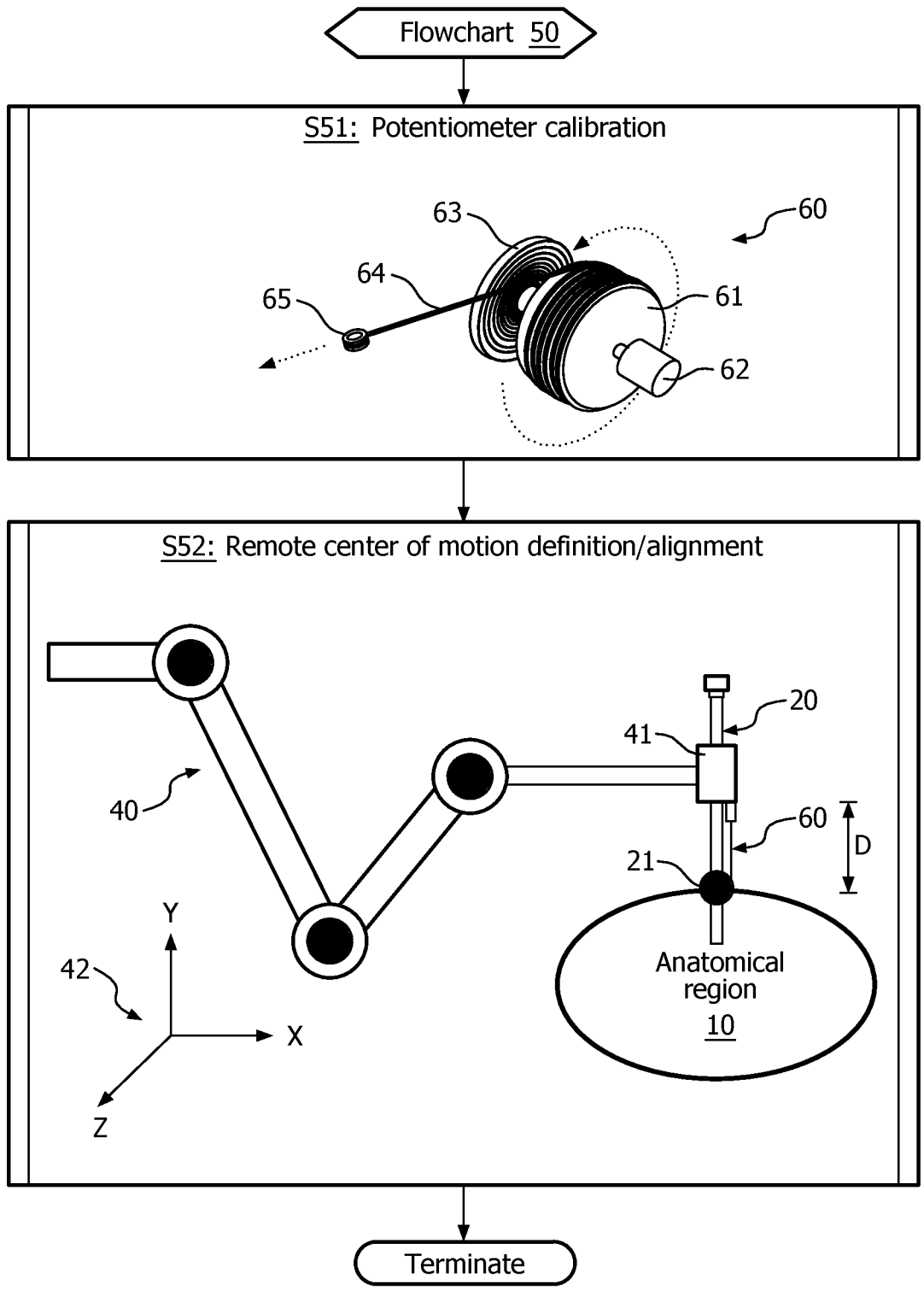
FIG. 4 illustrates a flowchart representative of an exemplary embodiment of a robotic surgical method in accordance with the present invention.

A flowchart 50 as shown in FIG. 4 is representative of robotic surgical method of the present invention directed to the use of a potentiometer to define the RCM for endoscope 20. Referring to FIG. 4, a stage S51 of flowchart 50 encompasses a calibration of a string potentiometer 60 that is mounted unto end effector 41 of endoscope 40. Potentiometer 60 employs a spool 61, a rotational sensor 62, a torsion spring 63, a flexible cable 64 and a coupler 65 as known in the art for providing a voltage proportional to an extension of cable 64 over a distance D. Upon being mounted on end effector 41, potentiometer 60 is registered in robotic coordinate system 42 as known in the art to thereby have a calibrated location within robotic coordinate system 42 as endoscope 20 is navigated via robot 20 within robotic coordinate system 42.

A stage S52 of flowchart 50 encompasses robot controller 43 calculating the distance D over which cable 64 has been extended to facilitate a determination of a virtual fulcrum point 21 of endoscope 20. In one embodiment of stage S52, cable 64 is pulled and attached via coupler 65 to a desired location of virtual fulcrum point 21 along endoscope 20 whereby the distance D together with the current joint positions of robot 40 are used conjunction with the robot kinematics by robot controller 43 to define the exact physical location of virtual fulcrum point 21 within robotic coordinate system 42. Thereafter, robot controller 43 commands robot 40 to navigate endoscope 20 whereby the physical location of virtual fulcrum point 21 within robotic coordinate system 42 partially or entirely coincides with the physical location of anatomical port 12 (FIG. 3) within robotic coordinate system 42.

In an alternative embodiment of stage S52, robot controller 43 commands robot 40 to navigate endoscope 20 whereby a desired location of virtual fulcrum point 21 within robotic coordinate system 42 partially or entirely coincides with anatomical port 12. Thereafter, cable 64 is pulled and attached via coupler 65 to the desired location of virtual fulcrum point 21 along endoscope 20 whereby the distance D together with the current joint positions of robot 40 are used conjunction with the robot kinematics by robot controller 43 to define the exact physical location of virtual fulcrum point 21 within robotic coordinate system 42.

Figure 5:
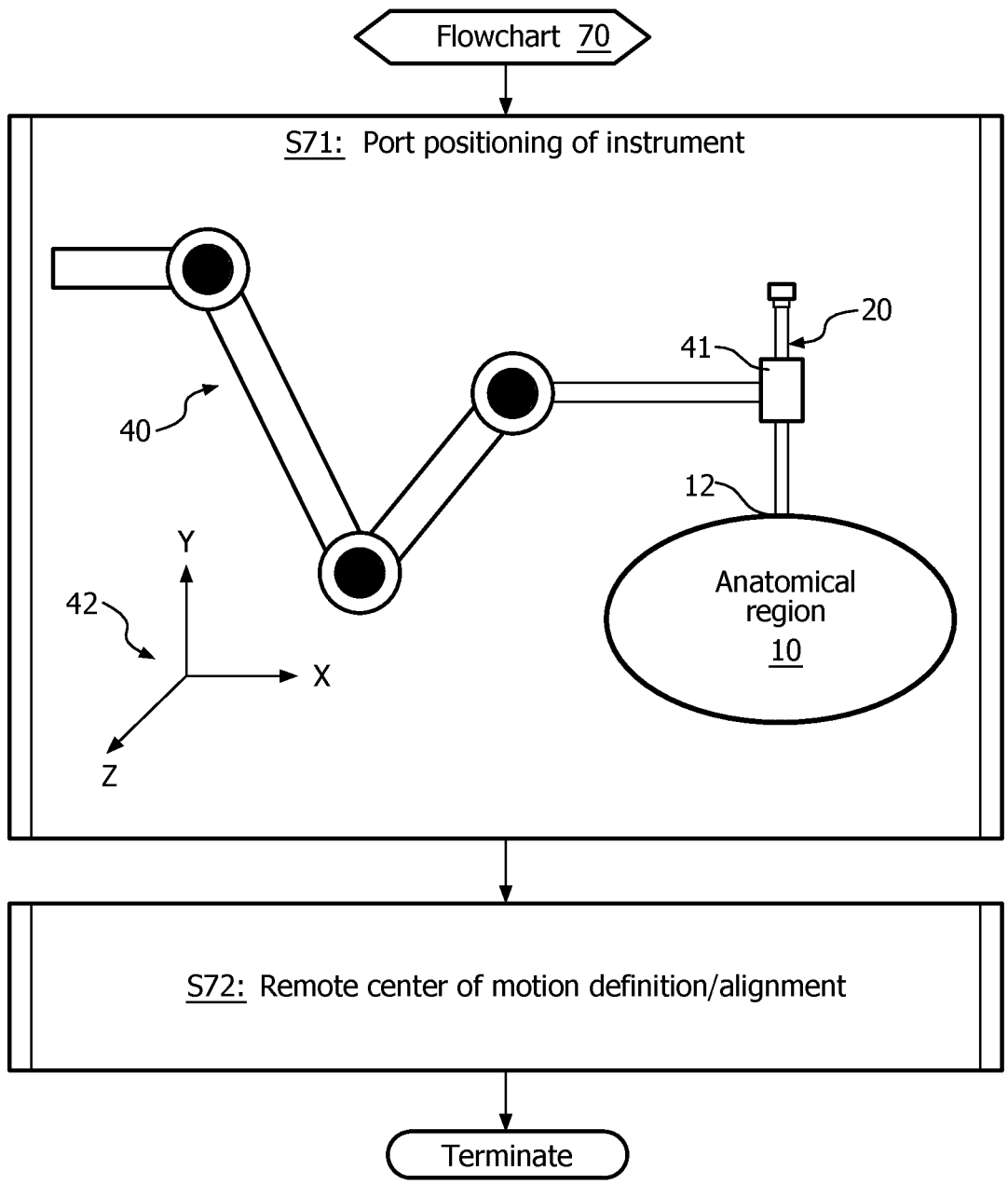
FIG. 5 illustrates a flowchart representative of an exemplary embodiment of a robotic surgical method in accordance with the present invention.

A flowchart 70 as shown in FIG. 5 is representative of robotic surgical method of the present invention directed to a use of locating distal tip 22 (FIG. 3) of endoscope 20 at the physical location of anatomical port 12. Referring to FIG. 5, a stage S71 of flowchart 70 encompasses robot controller 43 commanding robot 40 to navigate distal tip 22 of endoscope 20 to anatomical port 12 as known in the art whereby current joint positions of robot 40 are used conjunction with the robot kinematics by robot controller 43 to define the exact physical location of anatomical port 12 within robotic coordinate system 42.

Stage S72 of flowchart 70 encompasses robot controller 43 calculating a distance from anatomical port 12 to a desired virtual fulcrum point on endoscope 20. In practice, the distance D ranges from zero whereby the desired virtual fulcrum point coincides with the physical location of anatomical port 12 to a maximum distance between the distal tip of endoscope 20 and the end effector of robot 40. Based on the distance D from anatomical port 12 to a desired virtual fulcrum point on endoscope 20, the current joint positions of robot 40 with the distal tip of endoscope 20 at anatomical port 12 are used conjunction with the robot kinematics by robot controller 43 to define the exact physical location of virtual fulcrum point 21 within robotic coordinate system 42. As such, robot controller 43 commands robot 40 to endoscope 20 relative to anatomical port 12 whereby the virtual fulcrum point partially or entirely coincides with anatomical port 12.

Figure 6:
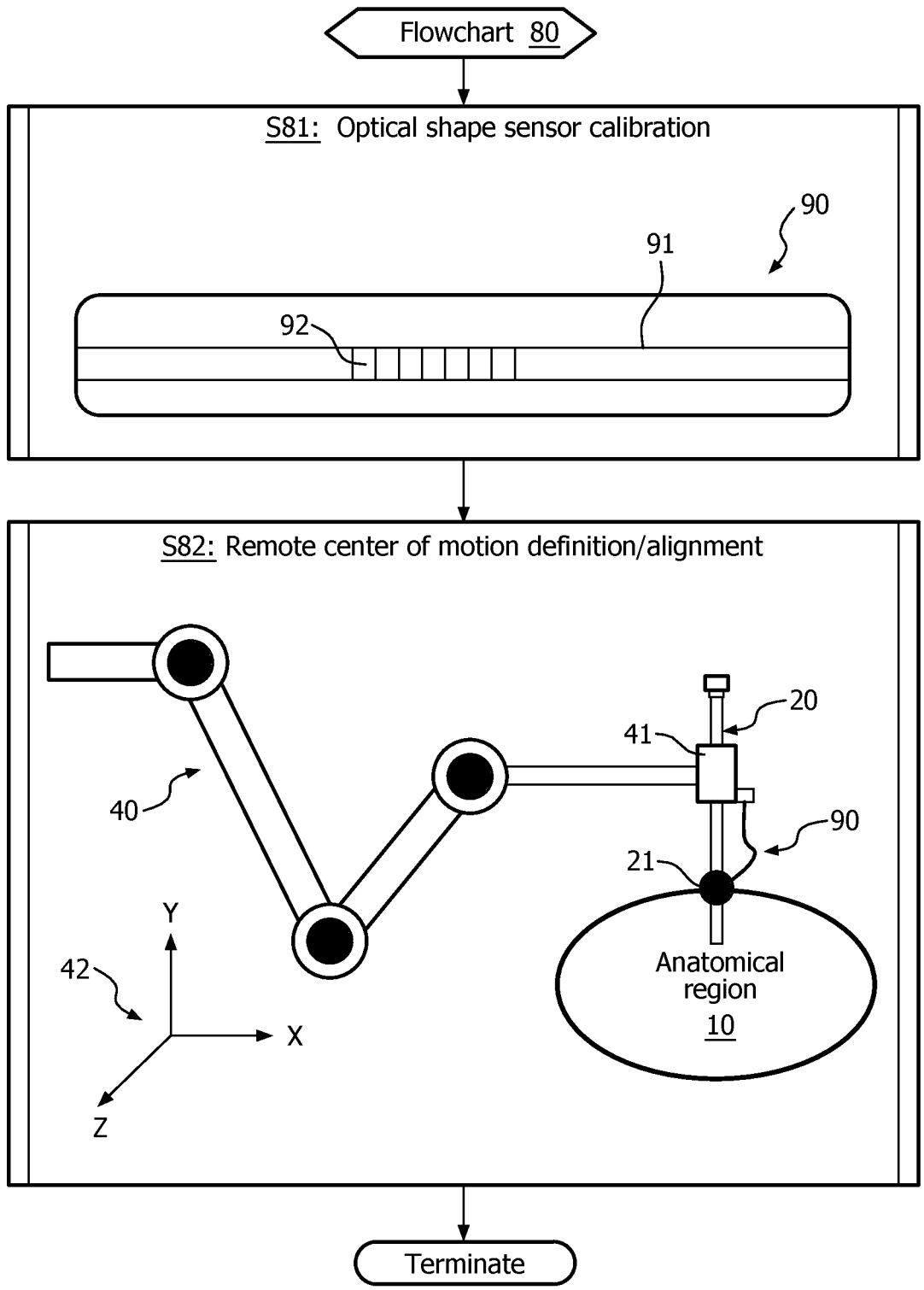
FIG. 6 illustrates a flowchart representative of an exemplary embodiment of a robotic surgical method in accordance with the present invention.

A flowchart 80 as shown in FIG. 6 is representative of robotic surgical method of the present invention directed to the use of a shape sensing optical fiber to define the RCM for endoscope 20. Referring to FIG. 6, a stage S81 of flowchart 80 encompasses a calibration of a shape sensing optical fiber 90 that is mounted unto end effector 41 of robot 40. Shape sensing optical fiber 90 employs Fiber Bragg Gratings 92 or other optical shape sensing capability within a fiber core 91 as known in the art for providing optical signals indicative of a shape of optical fibers 90 within robotic coordinate system 42. Upon having a proximal end mounted on end effector 41, shape sensing optical fiber 90 is registered in robotic coordinate system 42 as known in the art to thereby have a calibrated location within robotic coordinate system 42 as endoscope 20 is navigated via robot 40 within robotic coordinate system 42.

A stage S82 of flowchart 80 encompasses robot controller 43 calculating the distance D between the mounted proximal end of optical fiber 90 and a distal end of optical fiber 90 to facilitate a determination of a virtual fulcrum point 21 of endoscope 20. In one embodiment of stage S82, the distal end of optical fiber 90 is coupled to a desired location of virtual fulcrum point 21 along endoscope 20 whereby a sensed shape of optical fiber 90 as known in the art provides for the distance D, which together with the current joint positions of robot 40 are used conjunction with the robot kinematics by robot controller 43 to define the exact physical location of virtual fulcrum point 21 within robotic coordinate system 42. Thereafter, robot controller 43 commands robot 40 to navigate endoscope 20 whereby the physical location of virtual fulcrum point 21 within robotic coordinate system 42 partially or entirely coincides with the physical location of anatomical port 12 (FIG. 3) within robotic coordinate system 42.

In an alternative embodiment of stage S82, robot controller 43 commands robot 40 to navigate endoscope 40 whereby a desired location of virtual fulcrum point 21 within robotic coordinate system 42 partially or entirely coincides with anatomical port 12 (FIG. 5). Thereafter, the distal end of optical fiber 90 is coupled to the desired location of virtual fulcrum point 21 along endoscope 20 whereby the distance D (FIG. 4) together with the current joint positions of robot 40 are used conjunction with the robot kinematics by robot controller 43 to define the exact physical location of virtual fulcrum point 21 within robotic coordinate system 42.

Figure 7:
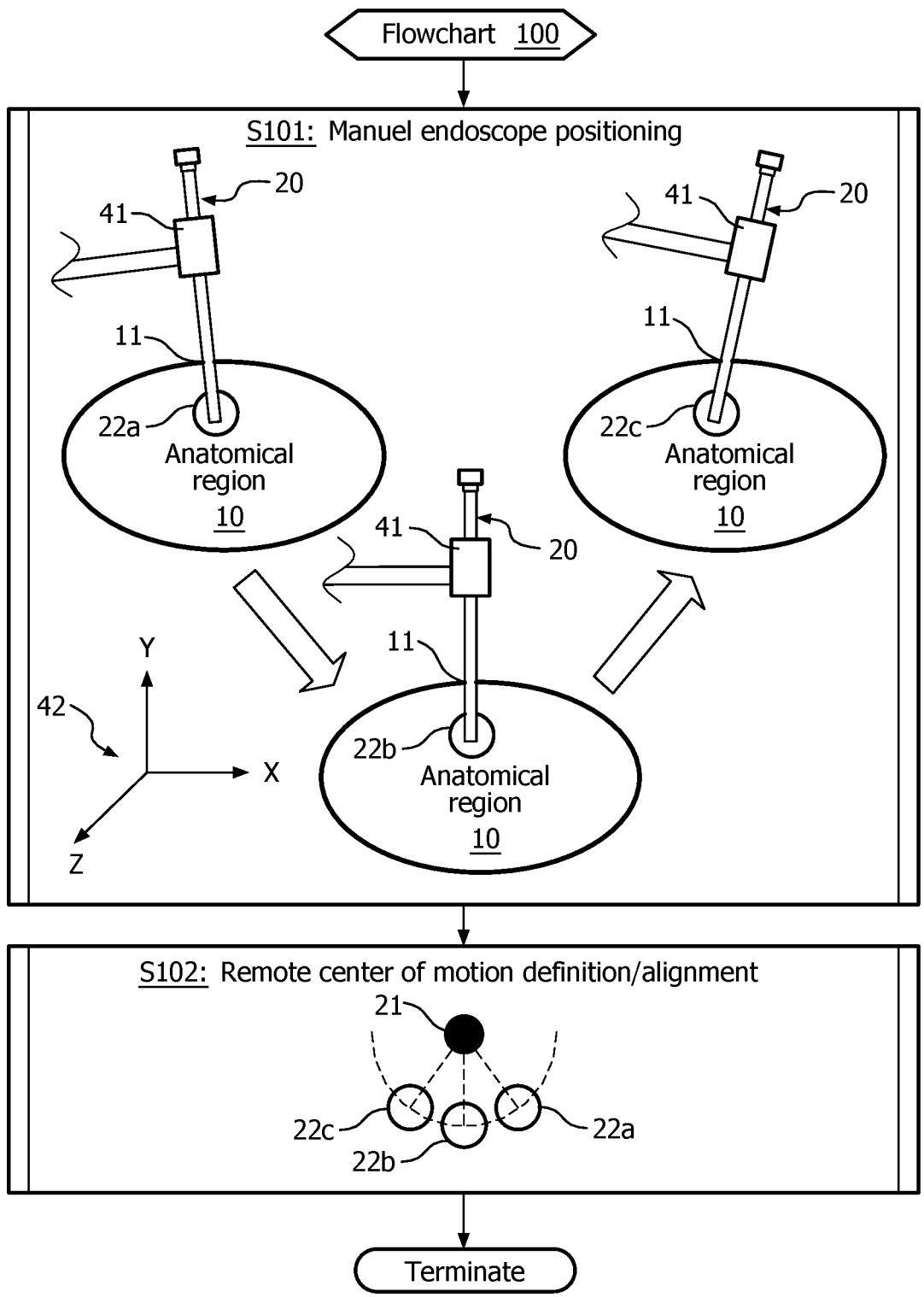
FIG. 7 illustrates a flowchart representative of an exemplary embodiment of a robotic surgical method in accordance with the present invention.

A flowchart 100 as shown in FIG. 7 is representative of robotic surgical method of the present invention directed locating distal tip 22 of endoscope 20 to a desired depth within anatomical region 10 to utilize compliance control of the robot and mathematical extraction of the remote center of motion. Specifically, force and torque sensors (not shown) located on robot 40 allows robot 40 to be manually moved with little or no effort. The compliance control works by using the force and torque sensors that sense the force a user exerts on the robot 40 and by using the dynamic model of robot 40 to convert those forces and torques into acceleration at the joints to thereby move robot 40.

Referring to FIG. 7, a stage S101 of flowchart 100 encompasses robot controller 43 commanding robot 40 to navigate distal tip 22 of endoscope 20 through anatomical port 11 to a desired depth as known in the art. Upon reaching the depth, the user slowly moves the robot in a manner that pivots endoscope 20 around the anatomical port as exemplary shown in FIG. 7. By obtaining the joint motions and calibrated positions 22a-22c of distal tip 22 of endoscope 20 and using forward kinematics during this motion, robot controller 43 mathematically calculates virtual fulcrum point 21 during a stage S102 of flowchart 100. In one embodiment of stage S102, the calibrated locations 22a-22c of distal tip 22 of endoscope 20 from time $t_0$ to $t_3$ as given by the robot kinematics is stored and their calibrated positions are used to solve an error minimization problem that finds the point 21 that is equidistant from all calibrated positions 22a-22c.

In practice, embodiments of a potentiometer and an optical fiber alternative to the embodiments shown in FIGS. 4 and 6 may be utilized in the implementation of a robotic surgical method of the present invention.

Again, in practice, robot controller 43 may be implemented by any configuration of hardware, software and/or firmware for executing the robotic surgical methods of the present invention, particularly the methods shown in FIGS. 4-7.

Also, in practice, any selection of a desired virtual fulcrum point is dependent upon many factors, such as, for example, a required depth of the surgical instrument into the anatomical region for purposes of performing a surgical task and the structural configuration of the surgical instrument relative to the anatomical structure of the patient.

From the description of FIGS. 1-7 herein, those having ordinary skill in the art will appreciate the numerous benefits of the present invention including, but not limited to, a robot controller capable of defining a virtual RCM for a surgical instrument (e.g., endoscope) mounted on an end-effector of a robot designed with or without a mechanical RCM.

Although the present invention has been described with reference to exemplary aspects, features and implementations, the disclosed systems and methods are not limited to such exemplary aspects, features and/or implementations. Rather, as will be readily apparent to persons skilled in the art from the description provided herein, the disclosed systems and methods are susceptible to modifications, alterations and enhancements without departing from the spirit or scope of the present invention. Accordingly, the present invention expressly encompasses such modification, alterations and enhancements within the scope hereof.

The invention claimed is:

1. A control unit for controlling a robotic surgical system including a robot operably configured to navigate a surgical instrument, the control unit comprising:
 a robot controller,
  wherein the robot controller is operably configured to define a remote center of motion for a spherical rotation of the surgical instrument of the robot at a target location within the coordinate system of the robot, and
  wherein the robot controller is further operably configured to command the robot to position the remote center of motion for the spherical rotation of the surgical instrument at the target location for spherically rotating the surgical instrument relative to the target location.

2. The control unit of claim 1, wherein:
defining the remote center of motion includes a calculation of a distance from a calibrated location of a potentiometer within the coordinate system of the robot to a physical location of a virtual fulcrum point of the instrument within the coordinate system of the robot established by an attachment of the potentiometer to an end effector of the robot and to the instrument; and
defining the remote center of motion of the instrument with a target location within the region includes the physical location of the virtual fulcrum point of the instrument within the coordinate system of the robot at least partially coinciding to the physical location of the target location within the region within the coordinate system of the robot.

3. The control unit of claim 1, wherein:
defining the remote center of motion includes a calculation of a distance from a calibrated location of a distal tip of the instrument within the coordinate system of the robot to a physical location of a virtual fulcrum point of the instrument within the coordinate system of the robot; and
aligning the remote center of motion of the instrument with a target location within the region includes the physical location of the virtual fulcrum point of the instrument within the coordinate system of the robot at least partially coinciding to the physical location of the target location within the region within the coordinate system of the robot.

4. The control unit of claim 1, wherein:
defining the remote center of motion includes a calculation of distance from a calibrated location of the optical fiber within the coordinate system of the robot to a physical location of a virtual fulcrum point of the instrument within the coordinate system of the robot established by an attachment of the optical fiber to an end effector of the robot and to the instrument; and
aligning the remote center of motion of the instrument with a target location within the region includes the physical location of the virtual fulcrum point of the instrument within the coordinate system of the robot at least partially coinciding to the physical location of the target location of the region within the coordinate system of the robot.

5. The control unit of claim 1, wherein the surgical instrument is an endoscope.

* * * * *